(12) United States Patent
Haldar et al.

(10) Patent No.: US 9,056,112 B2
(45) Date of Patent: Jun. 16, 2015

(54) PROCESS FOR PREPARATION OF PURE LINAGLIPTIN

(71) Applicant: DR. REDDY'S LABORATORIES LIMITED, Hyderabad (IN)

(72) Inventors: Pranab Haldar, Nutanbazar (IN); Venkateswarlu Muvva, Hyderabad (IN); Anil Kumar Prataprao, Visakhapatnam (IN); Vijaya Kumar Karri, Kakinada (IN); Bhanu Pratap Taduri, Hanamkonda (IN); Venkateshwara Natraj Birudaraju, Warangal (IN)

(73) Assignee: DR. REDDY'S LABORATORIES LIMITED, HYDERABAD (IN)

( * ) Notice: Subject to any disclaimer, the term of this patent is extended or adjusted under 35 U.S.C. 154(b) by 0 days.

(21) Appl. No.: 14/369,289

(22) PCT Filed: Dec. 27, 2012

(86) PCT No.: PCT/IB2012/057754
§ 371 (c)(1),
(2) Date: Jun. 27, 2014

(87) PCT Pub. No.: WO2013/098775
PCT Pub. Date: Jul. 4, 2013

(65) Prior Publication Data
US 2014/0357863 A1    Dec. 4, 2014

Related U.S. Application Data

(60) Provisional application No. 61/596,837, filed on Feb. 9, 2012.

(30) Foreign Application Priority Data

Dec. 28, 2011 (IN) ............................ 4633/CHE/2011

(51) Int. Cl.
*C07D 473/04* (2006.01)
*A61K 31/522* (2006.01)

(52) U.S. Cl.
CPC ............ *A61K 31/522* (2013.01); *C07D 473/04* (2013.01)

(58) Field of Classification Search
USPC ........................................................ 544/268
See application file for complete search history.

(56) References Cited

U.S. PATENT DOCUMENTS 7,407,955 B2    8/2008  Himmelsbach et al.

7,820,815 B2    10/2010  Pfrengle et al.
2011/0195917 A1   8/2011  Dugi et al.
2012/0129874 A1   5/2012  Sieger et al.

OTHER PUBLICATIONS

International Search Report dated May 30, 2013, for corresponding International Patent Application No. PCT/IB2012/057754.
Written Opinion dated May 30, 2013, for corresponding International Patent Application No. PCT/IB2012/057754.
International Preliminary Report on Patentability issued Jul. 1, 2014, for corresponding International Patent Application No. PCT/IB2012/057754.

*Primary Examiner* — Kristin Vajda
(74) *Attorney, Agent, or Firm* — Pergament Gilman & Cepeda LLP; Edward D. Pergament; Milagros A. Cepeda

(57) ABSTRACT

The present application provides a process for preparation of Linagliptin reacting (R)-piperidine-3-amine of Formula II or an acid addition salt thereof with 1-[(4-methyl-quinazolin-2-yl)methyl]-3-methyl-7-(2-butyn-1-yl)-8-bromoxanthine of Formula III in the presence of a suitable base in an inert organic solvent.

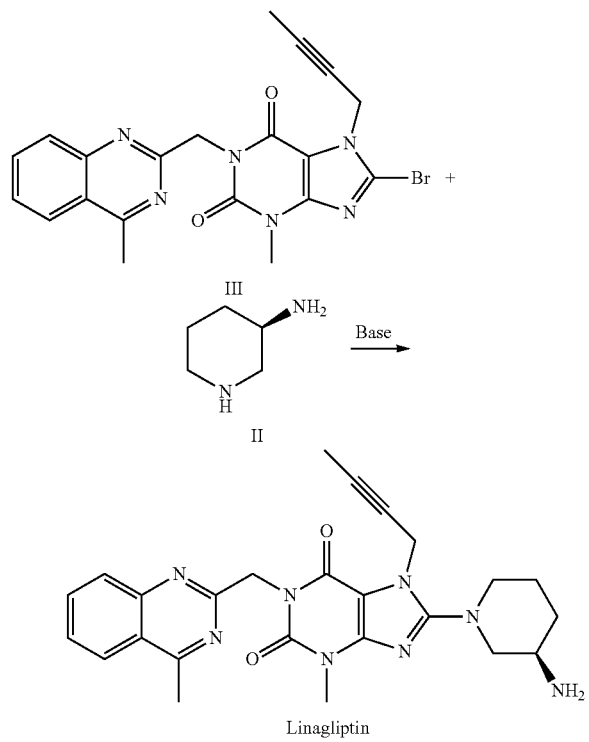

32 Claims, 4 Drawing Sheets

PROCESS FOR PREPARATION OF PURE LINAGLIPTIN

This application is a National Stage Application under 35 U.S.C. §371 of PCT International Application No. PCT/IB2012/057754 filed Dec. 27, 2012, which claims the benefit of U.S. Provisional Application No. 61/596,837, filed Feb. 9, 2012, and Indian Application No. 4633/CHE/2011, filed Dec. 28, 2011, all of which are hereby incorporated by reference in their entireties.

FIELD OF THE INVENTION

The present application relates to an improved process for preparation of Linagliptin.

BACKGROUND OF THE INVENTION

1-[(4-Methyl-quinazolin-2-yl)methyl]-3-methyl-7-(2-butyn-1-yl)-8-(3-(R)-amino-piperidin-1-yl) xanthine, whose international nonproprietary name is Linagliptin [CAS number: 668270-12-0], has the following chemical structure of formula I.

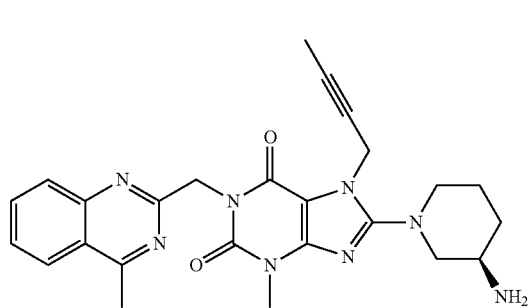

I

U.S. Pat. No. 7,407,955 (US '955) discloses Linagliptin, related compounds, and their pharmaceutical compositions. Further, it describes a process for the preparation of Linagliptin wherein tert-butyloxy carbonyl (Boc) protected Linagliptin is deprotected using 5-6 M isopropanolic hydrochloric acid followed by purification using chromatography. The process disclosed in US '955 is schematically represented in scheme-I.

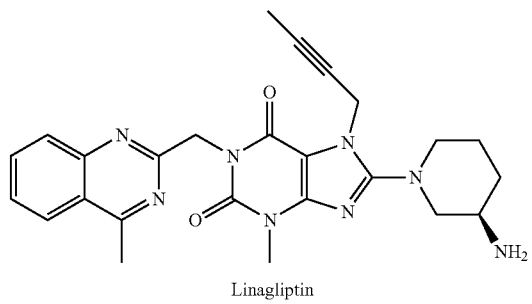

Linagliptin

U.S. Pat. No. 7,820,815 ("US '815) discloses a process for preparation of Linagliptin wherein it is prepared by deprotecting 1-[(4-methyl-quinazolin-2-yl)methyl]-3-methyl-7-(2-butyn-1-yl)-8-(3-(R)-phthalimidopiperidin-1-yl)-xanthine of formula IIIa in presence of ethanolamine. The 1-[(4-methyl-quinazolin-2-yl)methyl]-3-methyl-7-(2-butyn-1-yl)-8-(3-(R)phthalimidopiperidin-1-yl)-xanthine is prepared by condensing 1-[(4-methyl-quinazolin-2-yl)methyl]-3-methyl-7-(2-butyn-1-yl)-8-bromo xanthine of formula III with (R)-3-phthalimidopiperidine of formula IIa. The process disclosed in US '815 is schematically represented in scheme-II.

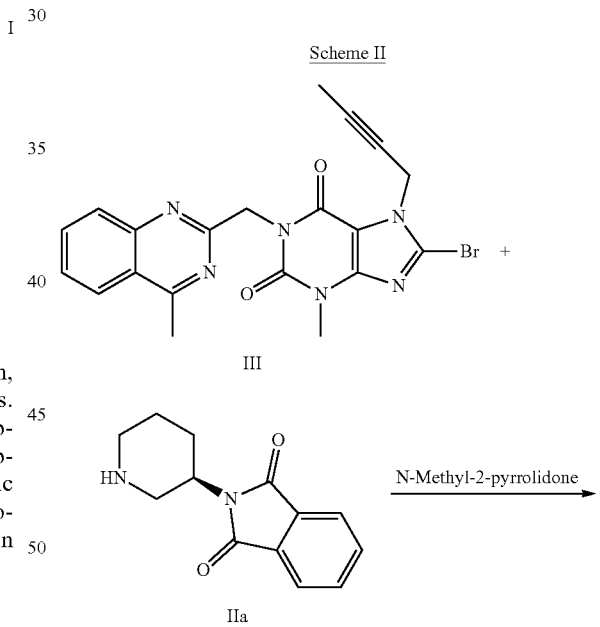

Scheme-I

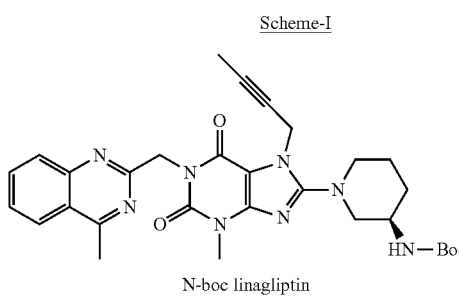

N-boc linagliptin

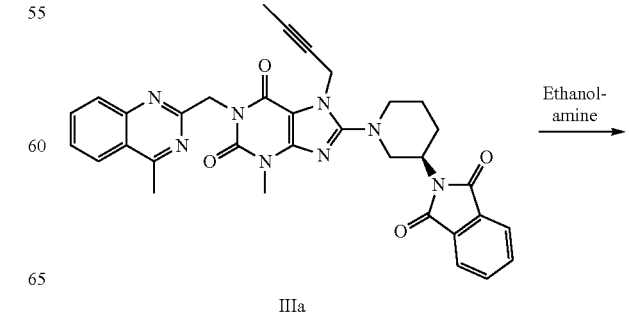

IIIa

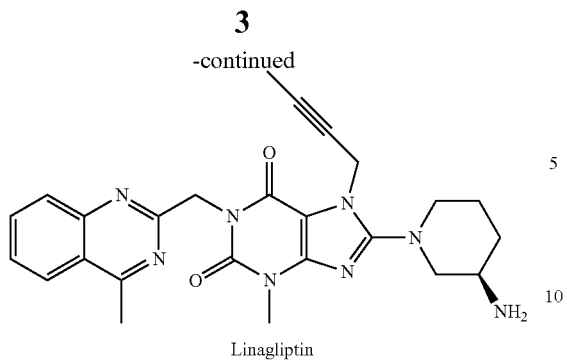

Linagliptin

The prior art processes as disclosed in US '955 and US '815 involve protection-deprotection method, leading to an increase in the manufacturing cycle time, decrease in the product yield and further requires purification by chromatography that is not desirable for commercial-scale manufacturing. In addition, the prior art processes leads to formation of bromo-butene impurity (i.e. 1-[(4-Methyl-quinazolin-2-yl) methyl]-3-methyl-7-(3-bromobut-2-ene-1-yl)-8-(3-(R)-amino-piperidin-1-yl) xanthine of formula Ib.

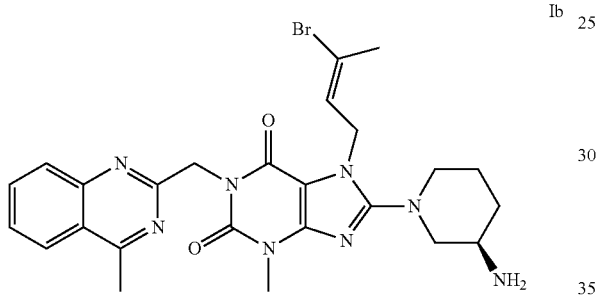

Ib

It is therefore essential to develop simplified and improved process for preparation of pure Linagliptin that alleviates the deficits of prior art processes. Thus, the present application provides an improved process for preparation of pure Linagliptin and pharmaceutically acceptable salts thereof.

SUMMARY

Aspects of the present application provide improved processes for preparing pure Linagliptin, acid addition salts and intermediates thereof.

In one aspect, the application provides a process for preparation of Linagliptin comprising reacting (R)-piperidine-3-amine of formula II or an acid addition salt thereof with 1-[(4-methyl-quinazolin-2-yl)methyl]-3-methyl-7-(2-butyn-1-yl)-8-bromoxanthine of formula III in the presence of a suitable base in an inert organic solvent.

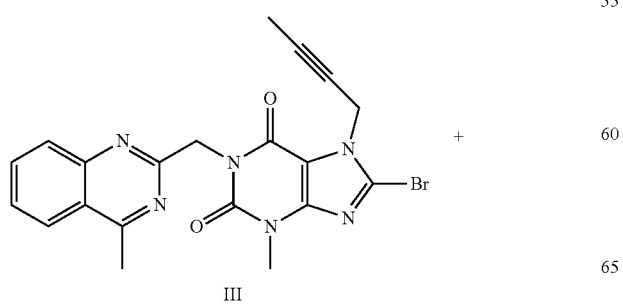

III

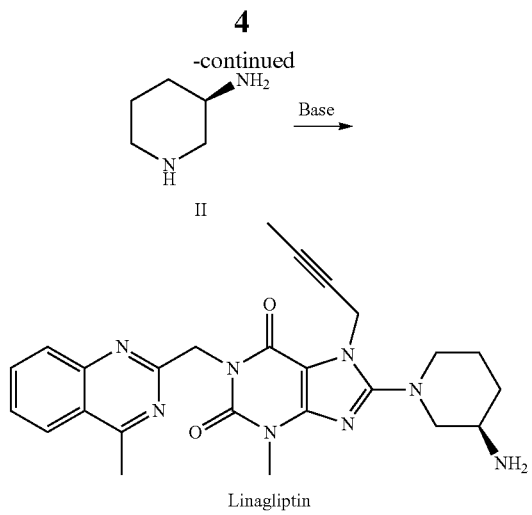

II

Linagliptin

In another aspect, the application provides Linagliptin or a pharmaceutically acceptable salt thereof, having less than about 0.15 area % of potential process related impurities viz., regio-impurity of the formula Ia, bromo-impurity of the formula Ib and S-isomer as measured by HPLC.

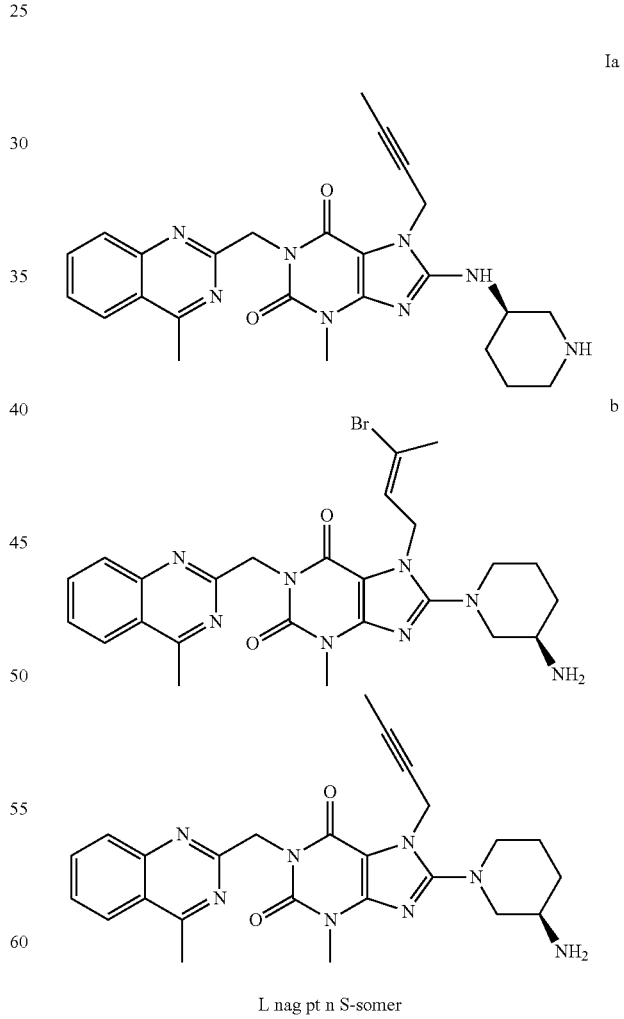

Linagliptin S-isomer

In another aspect, the application provides Linagliptin or a pharmaceutically acceptable salt thereof having a purity of greater than about 99.5 area % as measured by HPLC.

In another aspect, the application provides Linagliptin or a pharmaceutically acceptable salt thereof having less than about 0.5 area % of total impurities as measured by HPLC.

DETAILED DESCRIPTION

Figure 1:
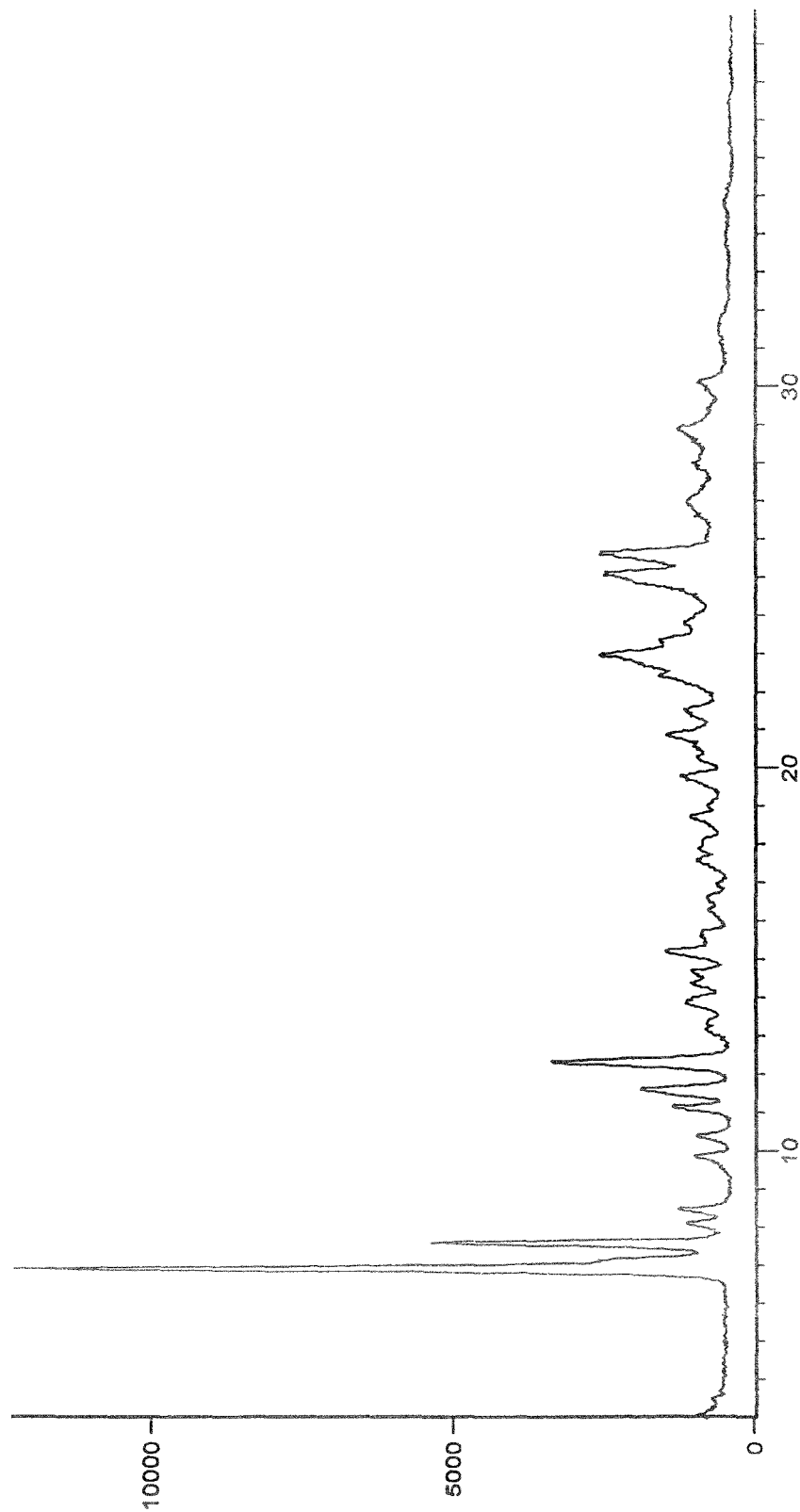
FIG. 1 is an illustration of a powder X-ray diffraction (PXRD) pattern of Linagliptin prepared according to Example 8(4).

Aspects of the present application provide processes for preparing pure Linagliptin and pharmaceutically acceptable salts thereof.

In one aspect, the application provides a process for preparation of Linagliptin comprising reacting (R)-piperidine-3-amine of formula II or an acid addition salt thereof with 1-[(4-methyl-quinazolin-2-yl)methyl]-3-methyl-7-(2-butyn-1-yl)-8-bromoxanthine of formula III in the presence a suitable base in an inert organic solvent.

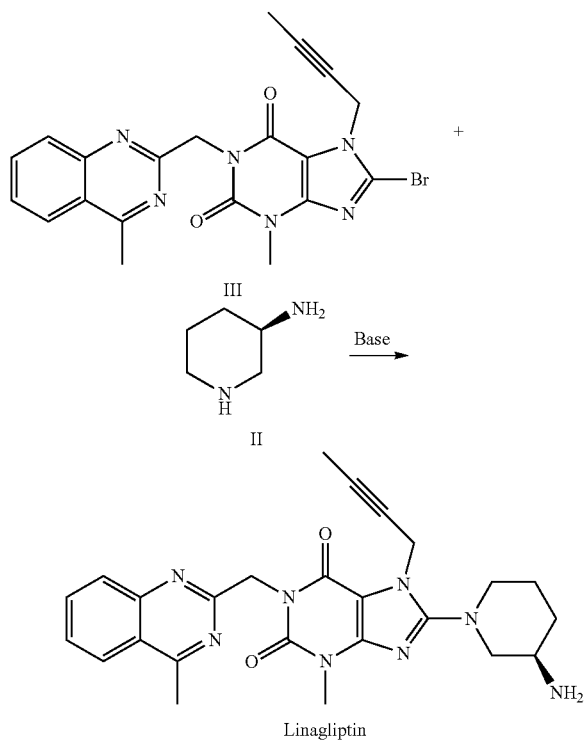

Preferably (R)-piperidine-3-amine of formula II is used as an acid addition salt like hydrochloride, hydrobromide, acetate, sulphate, dihydrochloride, tartrate, dibenzoyl tartrate and the like. In one embodiment the (R)-piperidine-3-amine of formula II is used as (R)-piperidine-3-amine dihydrochloride.

The base used in the reaction is an organic base or an inorganic base. Suitable organic bases that may be used, but are not limited to triethylamine, tributylamine, diisopropylethylamine (DIPEA), triisopropylamine, N-methyl morpholine, pyridine, 4-dimethylamino pyridine; In one embodiment the organic base is diisopropylethylamine (DIPEA) Suitable inorganic bases that may be used include, but are not limited to: alkali metal hydroxides such as lithium hydroxide, sodium hydroxide, potassium hydroxide, or the like; carbonates of alkali metals such as sodium carbonate, potassium carbonate, lithium carbonate, or the like; bicarbonates of alkali metals, such as lithium bicarbonate, sodium bicarbonate, potassium bicarbonate, or the like; ammonia; and any mixtures thereof; In one embodiment the inorganic base is potassium carbonate. The amount of base employed is not critical, but good practice recommends an amount of base from about an equimolar amount to about 5 times the equimolar amount with respect to the compound of formula III.

The reaction is effected in presence of a solvent. The solvents that can be used, include, but or not limited to, a ketone solvent such as acetone, methyl ethyl ketone, methylisobutylketone (MIBK) or the like; halogenated hydrocarbon solvent such as dichloromethane, ethylene dichloride, chloroform, or the like; aprotic polar solvents such as N,N-dimethylformamide (DMF), dimethylsulfoxide (DMSO), dimethylacetamide (DMA), acetonitrile or the like; ethers such as diethyl ether, tetrahydrofuran, methyl tetrahydrofuran, or the like; alcohols such as methanol, ethanol, 2-propanol, 2-butanol, or the like or mixtures thereof. In one embodiment the solvent is methylisobutylketone (MIBK). Quantities of solvent used for the process may be from about 1 mL to about 20 mL, per gram of compound of Formula II. In one embodiment the quantity is about 3 mL to about 15 mL, per gram of compound of Formula III.

The reaction is carried out at temperatures ranging from about 0° C. to about reflux temperature of the solvent used. In one embodiment the reaction is carried out at about 50° C. to about 100° C.

Surprisingly, it is found that if the reaction is carried out in presence of water the reaction is completed in less than 10 hours and the regio-impurity of the formula Ia and the bromo impurity of formula Ib are controlled to below 0.1% level. The amount of water used in the reaction is at least 1 wt % with respect to compound of formula III. In a preferred embodiment, the amount of water used in the reaction is about 2 wt % to about 10 wt % with respect to compound of formula III.

After completion of the reaction, the reaction mixture is filtered and the filtrate containing the linagliptin is treated with aqueous acid solution. The acids that can be used, include, but are not limited to a mineral acid such hydrochloric acid, phosphoric acid, sulphuric acid or the like; organic acids such as formic acid, acetic acid, citric acid, oxalic acid and the like. In one embodiment the acid is aqueous acetic acid. Concentration of the acid solution is from about 1% to about 20%. In a preferred embodiment the acid concentration is about 3% to about 10%. The aqueous layer containing the Linagliptin is washed with a water immiscible solvent such as dichloromethane, chloroform, ethylacetate, 2-butanol, toluene or the like or a mixture thereof.

The aqueous layer pH is adjusted to about 8 to about 12 using a suitable base such as sodium hydroxide, lithium hydroxide, potassium hydroxide or calcium hydroxide. The basic aqueous layer containing Linagliptin is extracted with a water immiscible solvent such as toluene, ethylacetate, dichloromethane or 2-butanol. In a preferred embodiment the water immiscible solvent is 2-butanol. The organic layer is concentrated completely to produce crude linagliptin.

The crude Linagliptin is converted to Linagliptin-D-(−)-tartrate by treating linagliptin in a suitable solvent or a mixture of solvents with D-(−)-tartaric acid. The solvent used for making Linagliptin-D-(−)-tartrate include, but are not limited to, water, lower alcohols such as methanol, ethanol, and isopropyl alcohol; esters such as ethyl acetate, methyl acetate, isopropyl acetate; ketones such as acetone, methylisobutylketone and the like, ethers such as tetrahydrofuran, dioxane, diethyl ether, methylisobutylether and the like. In a preferred embodiment the solvent is lower alcohol such as methanol, ethanol, and isopropyl alcohol.

The D-(−)-tartaric acid may be added as such or in the form of a solution and the resulting solution may be heated to about reflux temperature of the solvent. The solution is cooled to room temperature and maintained for about 30 minutes to about 10 hours and the Linagliptin-D-(−)-tartrate is isolated by filtration and is subjected to drying.

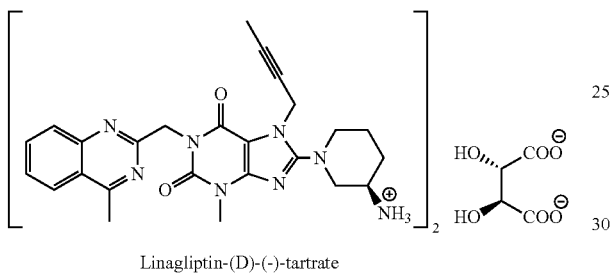

Linagliptin-(D)-(−)-tartrate

The isolated Linagliptin-D-(−)-tartrate can be present in any form which include but not limited to the crystalline or amorphous which may further be anhydrate, solvate, or hydrate. The isolated linagliptin D-(−)-tartrate may contain about 0.5% to about 10% of water. In one embodiment the isolated linagliptin D-(−)-tartrate is in crystalline form.

The crystalline Linagliptin-D-(−)-tartrate can be characterized by XRPD, DSC or TGA. In one embodiment crystalline Linagliptin-D-(−)-tartrate of present application is characterized by XRPD pattern comprising characteristic peaks at 2-theta angles of 4.14±0.2°, 7.17±0.2°, 7.45±0.2°, 8.28±0.2°, 9.02±0.2°, 9.49±0.2°, 10.36±0.2°, 10.78±0.2°, 11.54±0.2°, 12.58±0.2°, 13.60±0.2°, 14.51±0.2°, 17.76, ±0.2°, 18.45±0.2°, 19.48±0.2°, 20.70±0.2°, 21.11±0.2°, 21.69±0.2°, 23.66±0.2°, 24.19±0.2°, 25.24±0.2°, 25.64±0.2°, 26.05±0.2°, 26.67±0.2°.

Figure 4:
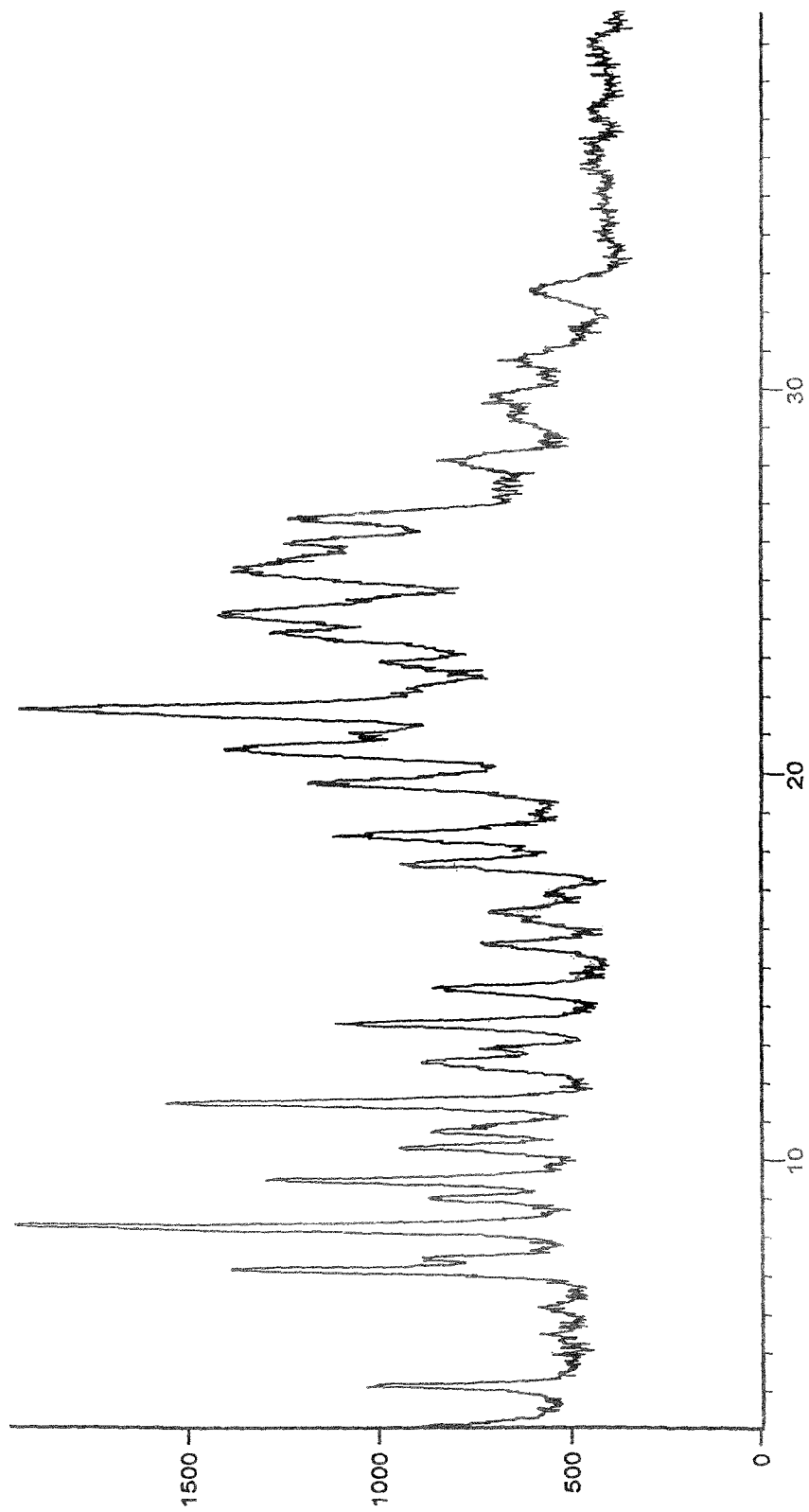
FIG. 4 is an illustration of a powder X-ray diffraction (PXRD) pattern of Linagliptin-(D)-tartrate prepared according to Example 12.

An illustrative XRPD pattern of Linagliptin-D-(−)-tartrate of the present application is shown in FIG. 4.

Pure Linagliptin is isolated from Linagliptin-D-(−)-tartrate using water and a suitable base. The Linagliptin-D-(−)-tartrate solution is treated with a suitable base such as lithium hydroxide, sodium hydroxide, potassium hydroxide or the like. The base may be added in the form of a solution having about 1% to about 20% concentration. The resulted solution is treated with a water immiscible organic solvent and the organic layer containing linagliptin is separated and is washed with water and concentrated to produce pure Linagliptin.

Linagliptin prepared by the processes herein described above is having a purity of greater than about 99 area % as measured by HPLC.

In another embodiment, the purity of Linagliptin produced by the process herein described above is greater than about 99.5 area % as measured by HPLC.

In another embodiment, the purity of Linagliptin produced by the processes herein described above is greater than about 99.8 area % as measured by HPLC.

In another embodiment, the application provides Linagliptin or a pharmaceutically acceptable salt thereof, produced by the process herein described above, having less than about 0.15 area % of each one of the potential process related impurities viz., regio-impurity of the formula Ia, bromo-impurity of the formula Ib and S-isomer as measured by HPLC.

L nag pt n S-somer

In another aspect, the present application provides the use of Linagliptin having a purity of greater than about 99.5 area % as measured by HPLC for the manufacture of a pharmaceutical composition.

In another aspect, the present application further provides the use of Linagliptin having less than 0.15 area % of total impurities as measured by HPLC for the manufacture of a pharmaceutical composition.

Linagliptin or a pharmaceutically acceptable salt thereof prepared by processes of the present invention as described above may advantageously be used in various pharmaceutical formulations for use in the treatment of type 2 diabetes and related diseases in accordance with the present invention. The present application therefor also relates to a pharmaceutical composition which comprises linagliptin prepared by processes of the present invention described above and a pharmaceutically acceptable carrier.

The pharmaceutical compositions of the invention comprising Linagliptin prepared by the processes of the present invention may further comprise one or more pharmaceutically acceptable excipients. Such excipients are preferably selected from the group consisting of fillers, sweeteners, buffering agents, glidants, flowing agents, flavoring agents, lubricants, preservatives, surfactants, wetting agents, binders, disintegrants and thickeners. Furthermore, the pharmaceutical composition may comprise a combination of two or more excipients also within one of the members of the above mentioned group.

In another aspect, the application provides a pharmaceutical combination comprising an effective amount of Linagliptin prepared by the processes of the present invention and Metformin or a pharmaceutically acceptable salt thereof. Furthermore the present application provides a pharmaceutical combination comprising an effective amount of linagliptin prepared by the processes of the present invention and Pioglitazone or a pharmaceutically acceptable salt thereof. In addition the present application provides a pharmaceutical combination comprising an effective amount of linagliptin prepared by the processes of the present invention and a Sulfonylurea or a pharmaceutically acceptable salt thereof.

Having described the invention with reference to certain preferred embodiments, other embodiments will become apparent to one skilled in the art from consideration of the specification. The disclosures of the references referred to in this patent application are incorporated herein by reference.

The invention is further defined by reference to the following examples describing in detail the processes of the invention. It will be apparent to those skilled in the art that many modifications, both to materials and methods, may be practiced without departing from the scope of the invention.

Definitions

The following definitions are used in connection with the present application unless the context indicates otherwise. Polymorphs are different solids sharing the same molecular formula, yet having distinct physical properties when compared to other polymorphs of the same formula. The abbreviation "MC" mean moisture content. Moisture content can be conveniently measured, for example, by the Karl Fischer method.

All percentages and ratios used herein are by weight of the total composition, unless the context indicates otherwise. All temperatures are in degrees Celsius unless specified otherwise and all measurements are made at 25° C. and normal pressure unless otherwise designated. The present disclosure can comprise the components discussed in the present disclosure as well as other ingredients or elements described herein.

As used herein, "comprising" means the elements recited, or their equivalents in structure or function, plus any other element or elements which are not recited. The terms "having" and "including" are also to be construed as open ended unless the context suggests otherwise.

Terms such as "about," "generally," "substantially," or the like are to be construed as modifying a term or value such that it is not an absolute. Such terms will be defined by the circumstances and the terms that they modify, as those terms are understood by those of skill in the art. This includes, at very least, the degree of expected experimental error, technique error and instrument error for a given technique used to measure a value.

In addition, where a reference is made to a figure, it is permissible to, and this document includes and contemplates, the selection of any number of data points illustrated in the figure which uniquely define that crystalline form, salt and/or optical isomer, within any associated and recited margin of error, for purposes of identification.

The polymorphic forms, produced by the methods of the present application can be analyzed by Powder X-ray Diffraction (PXRD) was performed on an X-ray Powder Diffractometer, equipped with a Cu-anode ($\lambda$=1.54 Angstrom), X-ray source operated at 45 kV, 40 mA, and a Ni filter is used to strip K-beta radiation. Two theta calibration is performed using an NIST SRM 640c Si standard. The sample was analyzed using the following instrument parameters: measuring range=2-50° 2θ, step width=0.017°; and measuring time per step 22 sec.

Linagliptin and its impurities can be analyzed using HPLC, such as with a liquid chromatograph equipped with a UV detector and the parameters described below:

| | |
|---|---|
| Column | Develosil ODS MG-5, 250 mm × 4.6 mm × 5 µm |
| Detector Wavelength | 225 nm |
| Flow rate | 1.0 mL/min |
| Temperature | 45° C. |
| Buffer Preparation | 0.02M $KH_2PO_4$. Adjust the pH to 3.5 with diluted ortho phosphoric acid solution and degas. |

Mobile phase A: Mixture of Buffer and Methanol in the ratio 900:100 (v/v)
Mobile phase B: Acetonitrile:Water:Methanol :: 700:150:150 (v/v)

| Elution gradient Program: | | | | | | | |
|---|---|---|---|---|---|---|---|
| | Time (minutes) | | | | | | |
| | 0.01 | 8 | 30 | 40 | 50 | 52 | 60 |
| Vol. % of mobile phase A | 75 | 75 | 45 | 25 | 25 | 75 | 75 |
| Vol. % of mobile phase B | 25 | 25 | 55 | 75 | 75 | 25 | 25 |

When a molecule or other material is identified herein as "pure", it generally means, unless specified otherwise, that the material is 99% pure or more, as determined by methods conventional in art such as high performance liquid chromatography (HPLC) or optical methods. In general, this refers to purity with regard to unwanted residual solvents, reaction byproducts, impurities, and unreacted starting materials. In the case of stereoisomers, "pure" also means 99% of one enantiomer or diastereomer, as appropriate. "Substantially" pure means, the same as "pure except that the lower limit is about 98% pure or more and likewise, "essentially" pure means the same as "pure" except that the lower limit is about 95% pure.

EXAMPLES

Example 1

Preparation of Linagliptin a) Preparation of 3-methyl-7-(2-butyn-1-yl)-8-bromo-xanthine (compound of formula IV)

3-Methyl-8-bromo-xanthine (30 gm) and N,N-dimethylformamide (170 mL) were charged into a 1000 mL round bottomed flask equipped with a mechanical stirrer. Diisopropylethylamine (DIPEA, 15.9 gm) and 1-bromo-2-butyne (16.2 gm) were added at 30° C. The reaction mixture was heated to 85° C. and maintained the temperature for 4 hours. The reaction mixture was cooled to 30° C. and pre cooled water (300 mL) was added. The solid formed was collected by filtration and washed with pre cooled water (150 mL) and diethyl ether (30 mL). The solid was dried in oven under vacuum at 50° C. to get 30.9 gm of the title compound.

(b) Preparation of 1-[(4-methyl-quinazolin-2-yl)methyl]-3-methyl-7-(2-butyn-1-yl)-8-bromoxanthine (compound of formula III)

3-Methyl-7-(2-butyn-1-yl)-8-bromo-xanthine (10 gm) and N,N-dimethylacetamide (150 mL) were charged into a 1000 mL round bottomed flask equipped with a mechanical stirrer. Potassium carbonate (9.3 gm) and 2-(chloromethyl)-4-methylquinazoline (6.8 gm) were added to the reaction mixture at room temperature. The reaction mixture was heated to 90° C. and maintained the temperature for 8 hours. The reaction mixture was cooled to 30° C. and water (450 mL) was added and the mixture was stirred for 1 hour at 30° C. The solid formed was collected by filtration and washed with water (150 mL). The wet cake was charged into 500 mL round bottomed flask and toluene (220 mL) was added and the mixture was heated to reflux temperature and maintained for 1 hour. The mixture was cooled to 10° C. and maintained for 2 hours. The solid was collected by filtration and washed with toluene (50 mL). The solid was dried in oven under vacuum at 80° C. to get 10.8 gm of the title compound. Purity by HPLC: 99.59%

(c) Preparation of Linagliptin

1-[(4-Methyl-quinazolin-2-yl)methyl]-3-methyl-7-(2-butyn-1-yl)-8-bromoxanthine (5 gm) and N,N-dimethylformamide (DMF, 50 mL) were charged into a 500 mL round bottomed flask equipped with a mechanical stirrer. Potassium carbonate (4.57 gm) and (R)-piperidine-3-amine dihydrochloride (2.86 gm) were added to the reaction mixture at room temperature. The reaction mixture was heated to 80° C. and maintained at that temperature for 8 hours. The reaction mixture was cooled to room temperature and DMF was evaporated under vacuum, then dichloromethane (DCM, 50 mL) was added, and stirred for 15 minutes. The reaction mixture was filtered to separate out the non-dissolved material and the non-dissolved material was washed with 15 mL of dichloromethane. The dichloromethane was evaporated under vacuum to give 4 gm of crude Linagliptin.

Example 2

One Pot Process for Preparation of Linagliptin

3-Methyl-8-bromo-xanthine (5 gm) and N,N-dimethylformamide (DMF, 28.5 mL) were charged into a 1000 mL round bottomed flask equipped with a mechanical stirrer. Diisopropylethylamine (DIPEA, 2.6 gm) and 1-bromo-2-butyne (2.7 gm) were added at 30° C. The reaction mixture was heated to 85° C. and maintained at this temperature for 4 hours. The reaction mixture is cooled to 30° C. and N,N-dimethylformamide (DMF, 100 mL) was added. Potassium carbonate (4.4 gm) and 2-(chloromethyl)-4-methylquinazoline (4.2 gm) were added to the reaction mixture at room temperature. The reaction mixture was heated to 85° C. and maintained at this temperature for 4 hours. The reaction mixture was cooled to 30° C. and N,N-dimethylformamide (DMF, 90 mL) was added. Potassium carbonate (8.3 gm) and (R)-piperidine-3-amine dihydrochloride (5.2 gm) were added to the reaction mixture at room temperature. The reaction mixture was heated to 80° C. and maintained at this temperature for 8 hours. The reaction mixture was cooled to 30° C. and DMF was evaporated under vacuum. Dichloromethane (DCM, 30 mL) was added and stirred for 15 minutes. The reaction mixture was filtered to separate out the undissolved material and the undissolved material was washed with dichloromethane (30 mL). The dichloromethane was evaporated under vacuum and 10% acetic acid (100 mL) was added. The resulted solution was stirred for 30 minutes and washed with dichloromethane (25 mL×3). The pH of the aqueous layer was adjusted to 8.5 with 10% aqueous sodium bicarbonate solution. The aqueous layer was extracted with dichloromethane (25 mL×2) and the dichloromethane was evaporated under vacuum to get 1.2 gm of Linagliptin.

Example 3

Preparation of Linagliptin

Figure 2:
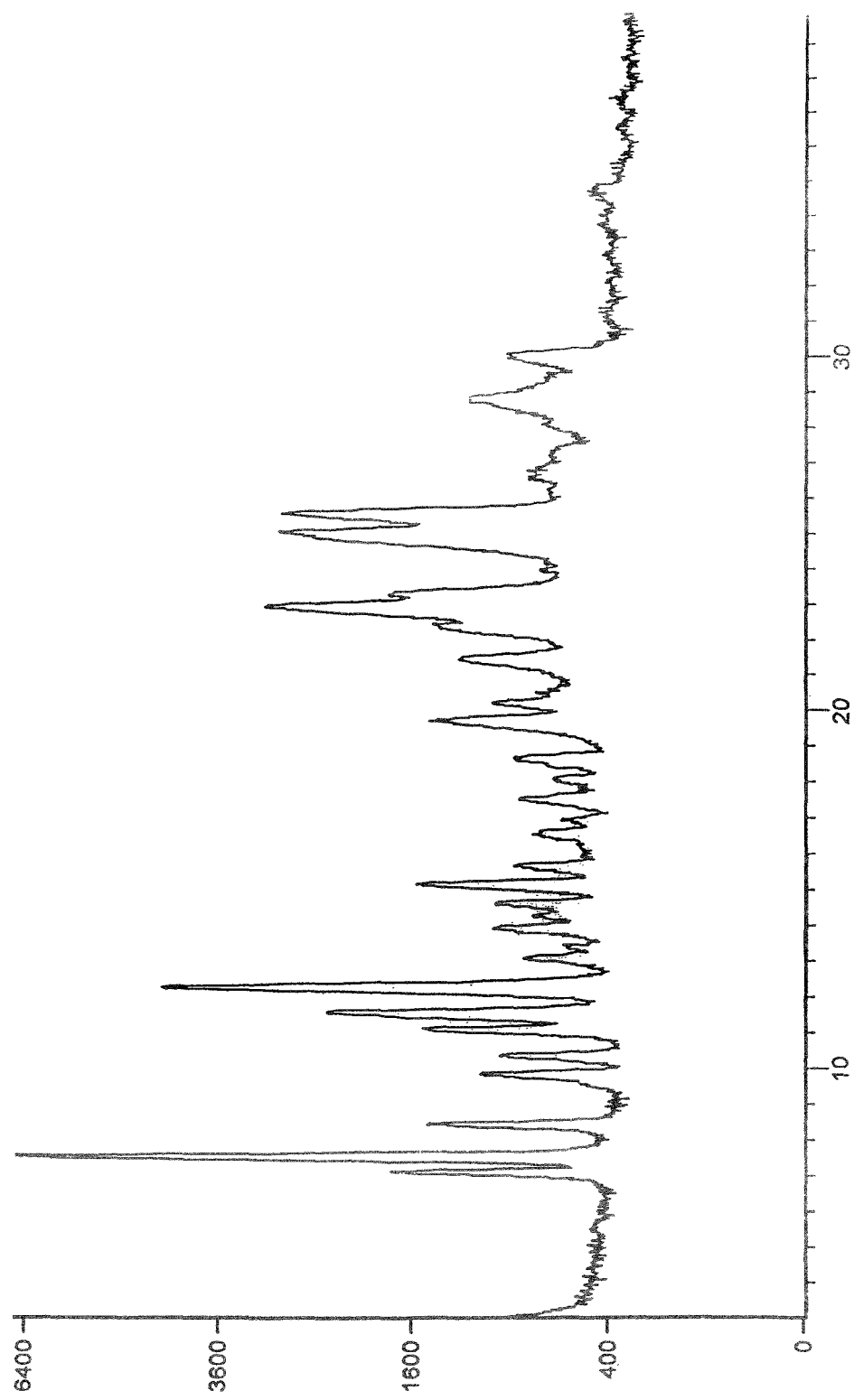
FIG. 2 is an illustration of a powder X-ray diffraction (PXRD) pattern of Linagliptin prepared according to Example 5.

1-[(4-Methyl-quinazolin-2-yl)methyl]-3-methyl-7-(2-butyn-1-yl)-8-bromoxanthine (20 gm) and methyl isobutyl ketone (MIBK 200 mL) were charged into a 1000 mL round bottomed flask equipped with a mechanical stirrer. Potassium carbonate (18.3 gm) and (R)-piperidine-3-amine dihydrochloride (11.5 gm) were added to the reaction mixture at 30° C. The reaction mixture was heated to 95° C. and maintained at that temperature for 8 hours. The reaction mixture was cooled to 30° C. and filtered and washed with MIBK (40 mL). The filtrate was charged into another flask and added 10% aqueous acetic acid solution and stirred for one hour at room temperature. The aqueous layer was separated and washed with 60 mL of dichloromethane. The aqueous layer was charged into another flask and 200 mL of dichloromethane and 100 mL of aqueous sodium hydroxide solution was added drop-wise at 30° C. The mixture was stirred for one hour at 30° C. and the organic layer was separated and the aqueous layer was extracted with 100 ml of dichloromethane. Combined the organic layers and evaporated under vacuum at below 45° C. Isopropyl alcohol (100 mL) was added to the residue and stirred for 3 hours at room temperature. Filtered the compound and washed with isopropyl alcohol (20 mL) and dried the compound at below 60° C. under vacuum to give 17.6 gm of Linagliptin. PXRD pattern: FIG. 2, Purity: 99.0%

Example 4

Preparation of Linagliptin

1-[(4-Methyl-quinazolin-2-yl)methyl]-3-methyl-7-(2-butyn-1-yl)-8-bromoxanthine (20 gm) and methyl isobutyl ketone (MIBK 200 mL) were charged into a 1000 mL round bottomed flask equipped with a mechanical stirrer. Potassium carbonate (18.3 gm) and (R)-piperidine-3-amine (11.5 gm) were added to the reaction mixture at room temperature. The reaction mixture was heated to 95° C. and maintained at that temperature for 8 hours. The reaction mixture was cooled to room temperature and filtered and washed with MIBK (40 mL). The filtrate was charged into another flask and added 10% aqueous acetic acid solution and stirred for one hour at room temperature. The aqueous layer was separated and washed with 60 mL of dichloromethane. The aqueous layer was charged into another flask and 200 mL of dichloromethane and 100 mL of aqueous sodium hydroxide solution (16 gm of sodium hydroxide in 100 mL of water) was added drop-wise at room temperature. The mixture was stirred for one hour at room temperature and the organic layer was separated and the aqueous layer was extracted with 100 ml of dichloromethane. Combined the organic layers and evaporated under vacuum at below 45° C. Hexane (100 mL) was added to the residue and stirred for 3 hours at 30° C. Filtered the compound and washed with Hexane (40 mL) and dried the compound at below 60° C. under vacuum to give 17.6 gm of Linagliptin. PXRD pattern: FIG. 2, Purity: 98.92%

Example 5

Preparation of Linagliptin

1-[(4-Methyl-quinazolin-2-yl)methyl]-3-methyl-7-(2-butyn-1-yl)-8-bromoxanthine (20 gm) and methyl isobutyl ketone (MIBK 200 mL) were charged into a 1000 mL round bottomed flask equipped with a mechanical stirrer. Potassium carbonate (18.3 gm) and (R)-piperidine-3-amine (11.5 gm) were added to the reaction mixture at 30° C. The reaction mixture was heated to 95° C. and maintained at that temperature for 8 hours. The reaction mixture was cooled to 30° C. and filtered and washed with MIBK (40 mL). The filtrate was charged into another flask and added 10% aqueous acetic acid solution and stirred for one hour at 30° C. The aqueous layer was separated and washed with 60 mL of dichloromethane. The aqueous layer was charged into another flask and 200 mL of dichloromethane and 100 mL of aqueous sodium hydroxide solution (16 gm of sodium hydroxide in 100 mL of water) was added drop-wise at 30° C. The mixture was stirred for one hour at 30° C. and the organic layer was separated and the aqueous layer was extracted with 100 ml of dichloromethane. Combined the organic layers and evaporated under vacuum at below 45° C. Toluene (100 mL) was added to the residue and stirred for 3 hours at 30° C. Filtered the compound and washed with Toluene (40 mL) and dried the compound at below 60° C. under vacuum to give 16.8 gm of Linagliptin. Purity: 98.91%, PXRD pattern: FIG. 2.

Example 6

Preparation of Linagliptin

1-[(4-Methyl-quinazolin-2-yl)methyl]-3-methyl-7-(2-butyn-1-yl)-8-bromoxanthine (20 gm) and methyl isobutyl ketone (MIBK 200 mL) were charged into a 1000 mL round bottomed flask equipped with a mechanical stirrer. Potassium carbonate (18.3 gm) and (R)-piperidine-3-amine (11.5 gm) were added to the reaction mixture at 30° C. The reaction mixture was heated to 95° C. and maintained at that temperature for 8 hours. The reaction mixture was cooled to 30° C. and filtered and washed with MIBK (40 mL). The filtrate was charged into another flask and added 10% aqueous acetic acid solution and stirred for one hour at 30° C. The aqueous layer was separated and washed with 60 mL of dichloromethane. The aqueous layer was charged into another flask and 200 mL of dichloromethane and 100 mL of aqueous sodium hydroxide solution (16 gm of sodium hydroxide in 100 mL of water) was added drop-wise at room temperature (pH is 10). The mixture was stirred for one hour 30° C. and the organic layer was separated and the aqueous layer was extracted with 100 ml of dichloromethane. Combined the organic layers and evaporated under vacuum at below 45° C. Ethyl acetate (100 mL) was added to the residue and stirred for 3 hours at 30° C. Filtered the compound and washed with ethyl acetate (40 mL) and dried the compound at below 60° C. under vacuum to give 17.6 gm of Linagliptin. PXRD pattern: FIG. 2, Purity: 98.72%

Example 7

Preparation of Linagliptin

1-[(4-Methyl-quinazolin-2-yl)methyl]-3-methyl-7-(2-butyn-1-yl)-8-bromoxanthine (4 gm) and methyl isobutyl ketone (MIBK 100 mL) were charged into a 1000 mL round bottomed flask equipped with a mechanical stirrer. Potassium carbonate (3.7 gm) and (R)-piperidine-3-amine dibenzoyl-D-tartrate (6.1 gm) were added to the reaction mixture at 26° C. The reaction mixture was heated to 100° C. and maintained at that temperature for 6 hours. The reaction mixture was cooled to 30° C. and filtered, and the salt was washed with MIBK (8 mL). The filtrate was charged into another flask and added slowly 10% aqueous acetic acid solution (40 mL) and stirred for one hour at 26° C. The aqueous layer was separated and washed with 12 mL of dichloromethane. The aqueous layer was charged into another flask and 40 mL of dichloromethane and 20 mL of 16% aqueous sodium hydroxide solution was added drop-wise at 26° C. The mixture was stirred for one hour at 26° C. and the organic layer was separated and the aqueous layer was extracted with 20 ml of dichloromethane. Combined the organic layers and evaporated under vacuum at below 45° C. Isopropyl alcohol (8 mL) was added to the residue and evaporated under vacuum at below 45° C. Isopropyl alcohol (16 mL) was added to the residue and stirred for 2 hours at 26° C. Filtered the compound and washed with isopropyl alcohol (4 mL) and dried the compound at 60° C. under vacuum to give 3.2 gm of Linagliptin. PXRD pattern: FIG. 2, Chemical Purity: 98.68%, Chiral Purity: 99.82%, S-isomer content: 0.12%, Regio impurity: 0.57%, Bromo impurity: 0.28%

Example 8

Preparation of Linagliptin

1-[(4-Methyl-quinazolin-2-yl)methyl]-3-methyl-7-(2-butyn-1-yl)-8-bromoxanthine (20 gm) and methyl isobutyl ketone (MIBK 200 mL) were charged into a 1000 mL round bottomed flask equipped with a mechanical stirrer. Potassium carbonate (18.3 gm) and (R)-piperidine-3-amine dihydrochloride (8.4 gm) were added to the reaction mixture at 26° C. The reaction mixture was heated to 100° C. and maintained at that temperature for 4 hours. The reaction mixture was cooled to 30° C. and filtered and washed with MIBK (40 mL). The filtrate was charged into another flask and added 200 mL of 10% aqueous acetic acid solution and stirred for 30 minutes at 28° C. The aqueous layer was separated and washed with 60 mL of dichloromethane. The aqueous layer was charged into another flask and 200 mL of dichloromethane and 100 mL of aqueous sodium hydroxide solution (16 gm of sodium hydroxide in 100 mL of water) were added drop-wise at 28° C. (pH is ≥10). The mixture was stirred for one hour at 28° C. and the organic layer was separated and the aqueous layer was extracted with 100 ml of dichloromethane. Combined the organic layers and divided into 5 equal parts.

Figure 3:
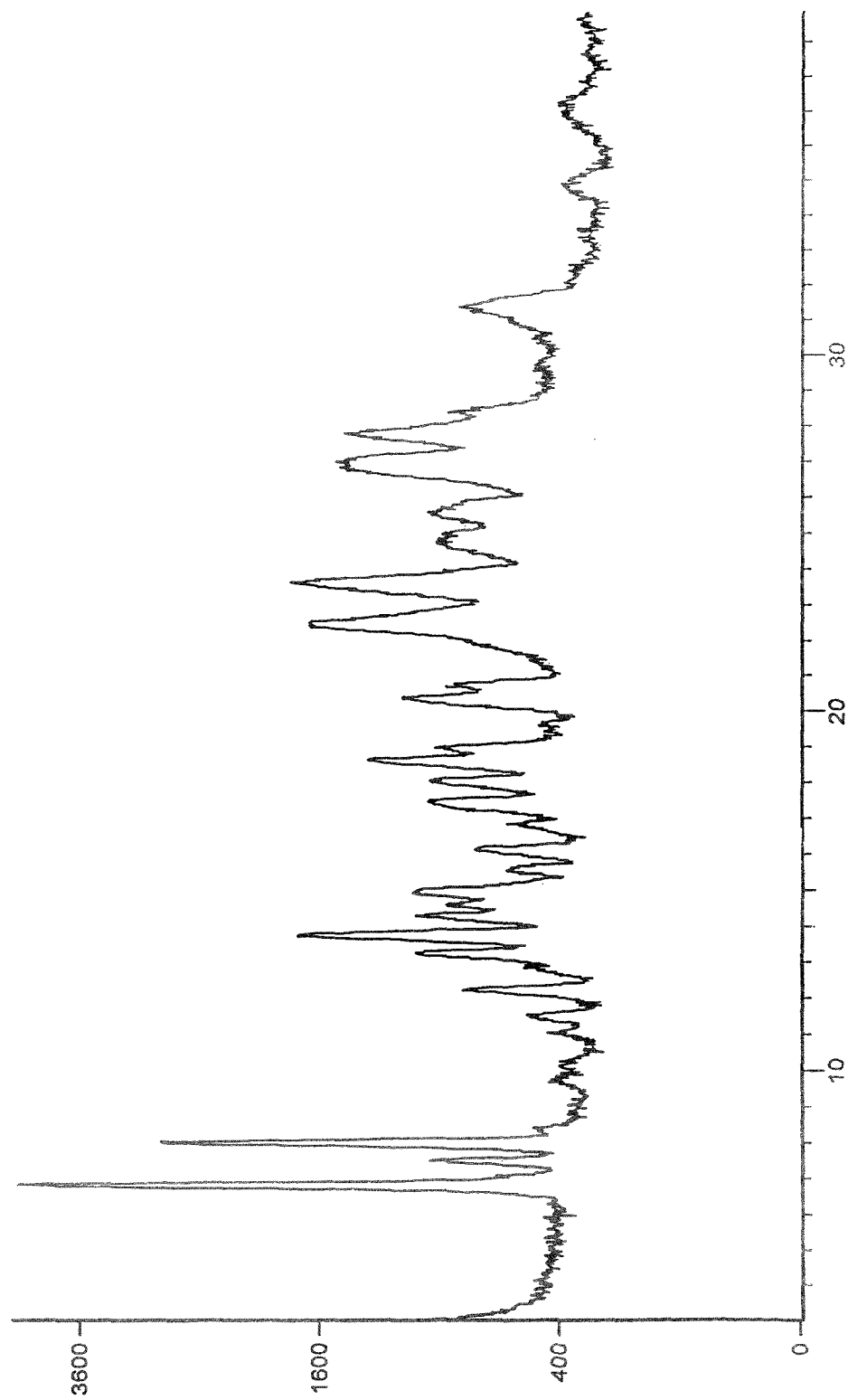
FIG. 3 is an illustration of a powder X-ray diffraction (PXRD) pattern of Linagliptin prepared according to Example 11.

Part 1: The organic layer was distilled off completely under vacuum at 45° C. Methanol (8 mL) was added to the residue and distilled off completely under vacuum at 45° C. Methanol (16 mL) was added to the residue stirred for 30 minutes at 28° C. and 48 mL of MTBE was added over a period of 30 minutes to the resulted solution at 27° C. and stirred for 1 hour. Filtered the compound and washed with 8 mL of MTBE and dried the compound at 65° C. under vacuum to give 3.0 gm of Linagliptin. PXRD pattern: FIG. 3. Chemical Purity: 99.46%, Regio impurity: 0.37%, Bromo impurity: 0.03%

Part 2: The organic layer was distilled off completely under vacuum at 45° C. Methanol (8 mL) was added to the residue and distilled off completely under vacuum at 45° C. Methanol (24 mL) was added to the residue stirred for 30 minutes at 28° C. and the resulted solution was cooled to 5°

C. and stirred for 1 hour. Filtered the compound and washed with 5 mL of chilled methanol and dried the compound at 65° C. under vacuum to give 3.0 gm of Linagliptin. PXRD pattern: FIG. 3. Chemical Purity: 99.41%, Regio impurity: 0.38%, Bromo impurity: 0.03%

Part 3: The organic layer was distilled off completely under vacuum at 45° C. Methanol (8 mL) was added to the residue and distilled off completely under vacuum at 45° C. Methanol (20 mL) was added to the residue stirred for 30 minutes at 28° C. and 20 mL of MTBE was added over a period of 30 minutes to the resulted solution at 27° C. and stirred for 1 hour. Filtered the compound and washed with 8 mL of MTBE and dried the compound at 65° C. under vacuum to give 2.8 gm of Linagliptin. PXRD pattern: FIG. 3. Chemical Purity: 99.47%, Regio impurity: 0.36%, Bromo impurity: 0.03%.

Part 4: The organic layer was distilled off completely under vacuum at 45° C. Isopropyl alcohol (8 mL) was added to the residue and distilled off completely under vacuum at 45° C. Methanol (16 mL) was added to the residue stirred for 30 minutes at 28° C. and 16 mL of isopropyl alcohol was added over a period of 30 minutes to the resulted solution at 27° C. and stirred for 1 hour. Filtered the compound and washed with 4 mL of isopropyl alcohol and dried the compound at 65° C. under vacuum to give 2.9 gm of Linagliptin. PXRD pattern: FIG. 1. Chemical Purity: 99.44%, Regio impurity: 0.38%, Bromo impurity: 0.02%.

Part 5: The organic layer was distilled off completely under vacuum at 45° C. Ethyl acetate (8 mL) was added to the residue and distilled off completely under vacuum at 45° C. Ethyl acetate (16 mL) was added to the residue stirred for 30 minutes at 28° C. and 16 mL of methanol was added over a period of 30 minutes to the resulted solution at 27° C. and stirred for 1 hour. Filtered the compound and washed with 4 mL of ethyl acetate and dried the compound at 65° C. under vacuum to give 0.7 gm of Linagliptin. PXRD pattern: FIG. 2. Chemical Purity: 99.57%, Regio impurity: 0.29%, Bromo impurity: 0.02%

Example 9

Purification of Linagliptin

Linagliptin (3.5 gm) was dissolved in 10% aqueous acetic acid and stirred for 15 minutes. Dichloromethane (50 mL) was added to the solution and stirred for 30 minutes. The aqueous layer was separated and the pH of this layer was adjusted to 8.5 using 10% aqueous sodium bicarbonate solution. The aqueous layer was extracted with dichloromethane (50 mL×2). The dichloromethane was evaporated under vacuum to give 3 gm of Linagliptin.

Example 10

Purification of Linagliptin

Linagliptin (31 gm) and methanol (124 mL) were charged into 500 mL round bottomed flask and the solution was heated to 40° C. and stirred for 60 minutes. Charcoal (3 gm) was added to the clear solution and stirred for 30 minutes. The solution was filtered through Hy-flow and the Hy-flow bed was washed with methanol (30 mL). Filtrate was charged into 1000 mL round bottomed flask and methyl tertiary butyl ether was added drop-wise to the solution and stirred for 2 hours at 30° C. The precipitate so formed was filtered and the wet cake was washed with methyl tertiary butyl ether (30 mL) to get 25.6 gm of pure Linagliptin. PXRD pattern: FIG. 3. Chemical Purity: 99.57%, Chiral purity: 99.73%, Regio impurity: 0.10%, Bromo impurity: 0.1%

Example 11

Purification of Linagliptin

Linagliptin (4 gm) and methanol (24 mL) were charged into 100 mL round bottomed flask and the solution is heated to 50° C. and stirred for 60 minutes. Methyl tertiary butyl ether (MTBE, 80mL) was charged into 500 mL round bottomed flask and the methanol solution containing linagliptin was added drop-wise at 27° C. and stirred for 2 hours at same temperature. The precipitate formed was filtered and the wet cake was washed with methyl tertiary butyl ether (8 mL) to get 2.6 gm of pure Linagliptin. PXRD pattern: FIG. 2, Bromo impurity content: 0.04%.

Example 12

Purification of Linagliptin a) Preparation of linagliptin-(D)-tartrate

Linagliptin (10 gm) and methanol (300 mL) were charged into 1000 mL round bottomed flask and (D)-tartaric acid solution (3.3 gm of (D)-tartaric acid in 100 mL of methanol) was added at 26° C. The solution was heated to 65° C. and stirred for 60 minutes. The solution was cooled to 28° C. and stirred for 2 hours at 27° C. The precipitate formed was filtered and the wet cake was washed with methanol (20 mL) and the solid was dried under vacuum at 55° C. to get 8.3 gm of Linagliptin-(D)-tartrate. PXRD pattern: FIG. 4. Chemical Purity: 99.72%, Chiral purity: 99.89%, Regio impurity: 0.08%, Bromo impurity: 0.05%, S-isomer: 0.11%.

b) Isolation of Pure Linagliptin

Linagliptin-(D)-tartrate (8 gm) and water (100 mL) were charged into 1000 mL round bottomed flask and stirred for 30 minutes at 26° C. Dichloromethane (80 mL) was added to the solution and cooled to 5° C. Aqueous sodium hydroxide solution (0.6 gm of NaOH is added to 20 mL of water) was added to the mixture at 5° C. and maintained for 1 hour. Layers were separated and aqueous layer was extracted with dichloromethane (20 mL). Combined both organic layers and dried over sodium sulphate and distilled off the organic layer under vacuum at 45° C. Hexane (20 mL) was added to the crude and stirred for 1 hour at 26° C. The precipitate was filtered and washed with 4 mL of hexane and dried the compound at 60° C. under vacuum to give 6 gm of pure Linagliptin. PXRD pattern: FIG. 2, Chemical Purity: 99.67%, Chiral purity: 99.85%, (S)-isomer content: 0.15%, Regio impurity: 0.09%, Bromo impurity: 0.07%.

Example 13

Preparation of (R)-piperidine-3-amine dihydrochloride (R)-piperidine-3-amine dibenzoyl-D-tartrate (9.0 gm) and isopropanol (50 mL) were charged in a 500 mL round bottomed flask equipped with a mechanical stirrer and water (4.5 mL) was added. The mixture was stirred for 30 minutes at 26° C. and IPA.HCl (18%, 12 mL) was added and the resulted mixture was heated to 62° C. and maintained for 2 hours at 62° C. Reaction mixture was allowed to get 26° C. and stirred for 20 hours at 26° C. The precipitation formed was filtered and washed with 9 mL of IPA. The solid was dried under vacuum at 70° C. to get 2.1 gm of pure (R)-piperidine-3-amine dihydrochloride. Chiral Purity: 99.87%, (S)-isomer content: 0.13%.

Example 14

Purification of (R)-piperidine-3-amine dihydrochloride (R)-piperidine-3-amine dihydrochloride (100 gm) and isopropanol (1500 mL) were charged in a 3000 mL round bottomed flask equipped with a mechanical stirrer and water (100 mL) was added. The mixture was heated to 70° C. and maintained for 2 hours at 70° C. Reaction mixture was allowed to get 28° C. and pure (R)-piperidine-3-amine dihydrochloride (1 gm) was added at same temperature. The mixture was stirred for 15 hours at 26° C. and the solid formed was filtered by suction and washed with isopropanol (100 mL). The solid was dried under vacuum at 60° C. to get 65.2 gm of pure (R)-piperidine-3-amine dihydrochloride.
Chiral Purity: 99.9%, (S)-isomer content: 0.09%.

Example 15

Preparation of 1-[(4-Methyl-quinazolin-2-yl)methyl]-3-methyl-7-(2-butyn-1-yl)-8-bromoxanthine (compound of Formula III)

3-Methyl-7-(2-butyn-l-yl)-8-bromo-xanthine (10 gm) and N,N-dimethylacetamide (150 mL) were charged into a 1000 mL round bottomed flask equipped with a mechanical stirrer. Potassium carbonate (10.7 gm) and 2-(chloromethyl)-4-methylquinazoline (7.1 gm) were added to the reaction mixture at room temperature.
The reaction mixture was heated to 98° C. and maintained the temperature for 8 hours. The reaction mixture was cooled to 30° C. and water (450 mL) was added and the mixture was stirred for 1 hour at 30° C. The solid formed was collected by filtration and washed with water (150 mL). The wet cake was charged into 500 mL round bottomed flask and toluene (220 mL) was added and the mixture was heated to reflux temperature and maintained for 1 hour. The mixture was cooled to 10° C. and maintained for 3 hours. The solid was collected by filtration and washed with toluene (5 mL). The solid was dried in oven under vacuum at 77° C. to get 12.1 gm of the title compound.
Purity by HPLC: 98.22%.

Example 16

Purification of Linagliptin (a) Preparation of linagliptin-D-(−)-tartrate

1-[(4-Methyl-quinazolin-2-yl)methyl]-3-methyl-7-(2-butyn-1-yl)-8-bromoxanthine (100 gm) and methyl isobutyl ketone (MIBK, 1000 mL) were charged into a 2000 mL round bottomed flask equipped with a mechanical stirrer. Potassium carbonate (76.1 gm), (R)-piperidine-3-amine dihydrochloride (45.8 gm) and water (5 mL) were added to the reaction mixture at 26° C. The reaction mixture was heated to 95° C. and maintained at that temperature for 6 hours. The reaction mixture was cooled to 30° C. and water (5 mL) was added to the reaction mixture and heated to 95° C. and maintained for 5 hours. The reaction mixture was filtered and washed with MIBK (200 mL). The filtrate was charged into another flask and added 1000 mL of 6% aqueous acetic acid solution and stirred for 30 minutes at 28° C. The aqueous layer was separated and washed with 300 mL of toluene and 100 mL of 2-butanol. The aqueous layer was charged into another flask and 1000 mL of 2-butanol and 325 mL of 9% aqueous sodium hydroxide solution were added drop-wise at 28° C. (pH is 10.25). The mixture was stirred for one hour at 28° C. and the organic layer was separated and the aqueous layer was extracted with 500 ml of 2-butanol. The combined 2-butanol layers were concentrated and 250 mL of 2-butanol was added to the residue and the resulted solution was concentrated. 400 mL of methanol was added to the residue and the resulted solution was heated to 48° C. and stirred for 1 hour at 48° C. The solution was cooled to 28° C. and 0.5 gm of linagliptin was seeded and the solution was cooled to 5° C. and maintained for 2 hours. The precipitation formed was filtered and washed with 100 mL of 2-butanol. The wet compound and 2500 mL were charged into 5000 mL round bottomed flask and the solution was heated to 40° C. and D-(−)-tartaric acid solution (19.9 gm of D-(−)-tartaric acid in 500 mL of methanol) was added slowly over a period of 30 minutes at 45° C. the resulted solution was heated to reflux and stirred for 30 minutes. The solution was cooled to 12° C. and stirred for 3 hours. The precipitation formed was filtered and washed with 100 mL of methanol to get 172 gm of wet compound. The wet compound was dried under vacuum at 70° C. for 7 hours to get 79.5 gm of Linagliptin-D-(−)-tartrate. XRPD pattern: FIG. 4, Chiral Purity: 99.96%, Regio impurity: 0.08%, Bromo impurity: 0.05%, (S)-isomer content: 0.04%, Tartaric acid content: 16.7%, Water content: 4.64%.

(b) Isolation of Pure Linagliptin

Linagliptin-D-(−)-tartrate (45 gm), water (675 mL) and toluene (900 mL) were charged into 5000 mL round bottomed flask and stirred for 10 minutes at 28° C. The resulted solution was heated to 45° C. and 45 mL of 9% aqueous sodium hydroxide solution was added to the mixture at 45° C. (pH is 11.30) and maintained for 1 hour. Layers were separated and organic layer was washed with water (225 mL×2). Combined the organic layers and distilled off the organic layer under vacuum at 45° C. to give 35.4 gm of linagliptin.
Chemical Purity: 99.86%, Chiral purity: 99.97%, (S)-isomer content: 0.03%, Regio impurity: 0.08%, Bromo impurity: 0.05%.

The invention claimed is:
1. A process for preparation of Linagliptin comprising reacting (R)-piperidine-3-amine of formula II or an acid addition salt thereof with 1-[(4-methyl-quinazolin-2-yl)methyl]-3-methyl-7-(2-butyn-1-yl)-8-bromoxanthine of formula III in presence of a suitable base in an inert organic solvent

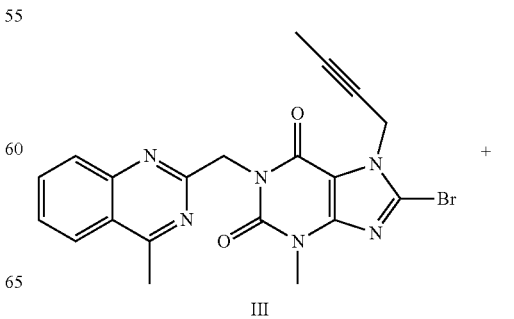

III

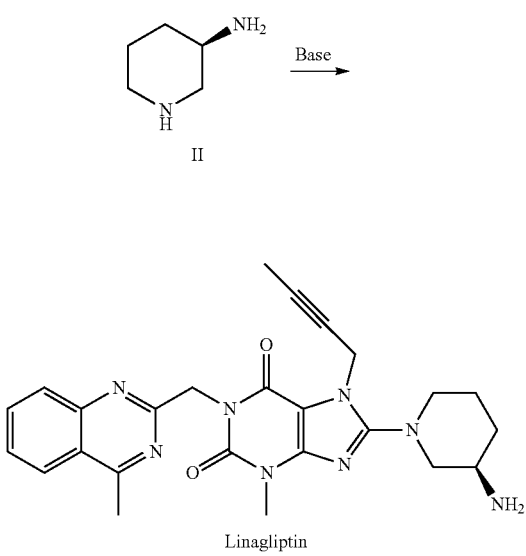

Linagliptin

2. The process according to claim 1, the reaction is carried out in the presence of water.

3. The process according to claim 2, wherein water used is at least about 1 wt % with respect to compound of formula III.

4. The process according to claim 2, wherein water used is about 2 wt % to about 10 wt % with respect to compound of formula III.

5. The process according to claim 1, wherein the organic solvent is selected from the group comprising of an alcohol solvent, a ketone solvent, a hydrocarbon solvent, a halogenated hydrocarbon solvent, an aprotic polar solvent, an ether solvent, or mixtures thereof.

6. The process according to claim 5, wherein the aprotic polar solvent is selected from the group comprising of dimethylformamide (DMF), dimethylsulfoxide (DMSO) and acetonitrile.

7. The process according to claim 5, wherein the ketone solvent is selected from the group comprising of acetone, methyl ethyl ketone and methylisobutylketone.

8. The process according to claim 5, wherein the ketone solvent is methylisobutylketone.

9. The process according to claim 1, wherein (R)-piperidine-3-amine of formula II is used in the form of a salt.

10. The process according to claim 9, wherein the salt of (R)-piperidine-3-amine is selected from the group comprising of hydrochloride, hydrobromide, acetate, sulphate, dihydrochloride, tartrate, dibenzoyl tartrate.

11. The process according to claim 9, wherein the salt of (R)-piperidine-3-amine is (R)-piperidine-3-amine dihydrochloride.

12. The process according to claim 1, further comprises:
(a) treating the reaction mixture of claim 1 with a suitable acid to form a solution,
(b) optionally washing the solution of step (a) with a water immiscible solvent,
(c) treating the solution of step (a) or (b) with a suitable base,
(d) extracting Linagliptin from the solution of step (c) with a suitable solvent,
(e) isolating Linagliptin.

13. The process according to claim 12, wherein the acid used in step (a) is selected from the group comprising of hydrochloric acid, acetic acid and sulphuric acid.

14. The process according to claim 12, wherein the acid used in step (a) is acetic acid.

15. The process according to claim 12, wherein the water immiscible solvent used in step (b) is selected from the group comprising of ethyl acetate, hexane, ether, toluene, and 2-butanol.

16. The process according to claim 12, wherein the base used in step (c) is selected from the group comprising of lithium hydroxide, sodium hydroxide, potassium hydroxide or calcium hydroxide.

17. The process according to claim 12, wherein the base used in step (c) is sodium hydroxide.

18. The process according to claim 12, wherein the solvent used in step (d) is selected from the group comprising of toluene, ethylacetate, 2-butanol chloroform, and dichloromethane.

19. The process according to claim 12, further comprises:
(a) converting the Linagliptin into Linagliptin-D-(−)-tartrate salt in a suitable solvent,
(b) treating the Linagliptin-D-(−)-tartrate salt with a suitable base to obtain a solution containing Linagliptin,
(c) extracting Linagliptin from the solution of step (b) with a suitable solvent,
(d) isolating pure Linagliptin.

20. The process according to claim 19, wherein the solvent used in step (a) is selected from the group comprising of methanol, ethanol, 2-propanol, toluene, ethylacetate, 2-butanol, dichloromethane water or mixtures thereof.

21. The process according to claim 19, wherein the solvent used in step (a) is methanol.

22. The process according to claim 19, wherein the base used in step (b) is selected from the group comprising lithium hydroxide, sodium hydroxide, potassium hydroxide or calcium hydroxide.

23. The process according to claim 19, wherein the base used in step (b) is sodium hydroxide.

24. The process according to claim 19, wherein the solvent used in step (c) is selected from the group comprising of toluene, ethylacetate, 2-butanol chloroform, and dichloromethane.

25. The process according to claim 19, wherein the solvent used in step (c) is 2-butanol.

26. The process according to claim 19, wherein the Linagliptin-D-(−)-tartrate formed in step (a) is a hemi-tartrate.

27. The process according to claim 19, wherein the Linagliptin-D-(−)-tartrate contains about 1 wt % to about 10 wt % of water.

28. The process according to claim 19, wherein the Linagliptin-D-(−)-tartrate contains about 3 wt % to about 5 wt % of water.

29. The process according to claim 19, wherein the Linagliptin-D-(−)-tartrate is in crystalline form.

30. The process according to claim 29, wherein the Linagliptin-D-(−)-tartrate is characterized by an X-ray powder diffraction pattern comprising at 2-theta angle 4.14±0.2°, 7.17±0.2°, 7.45 v, 8.28±0.2°, 9.02±0.2°, 9.49±0.2°, 10.36±0.2°, 11.54±0.2°, 13.60±0.2°, 20.70±0.2°, 21.69±0.2°.

31. The process according to claim 1, wherein Linagliptin is obtained with a HPLC purity greater than 99.5%.
32. The process according to claim 1, wherein Linagliptin obtained is having less than about 0.15 area % of regio-impurity of the formula Ia, bromo-impurity of the formula Ib and S-isomer as measured by HPLC.
Ia
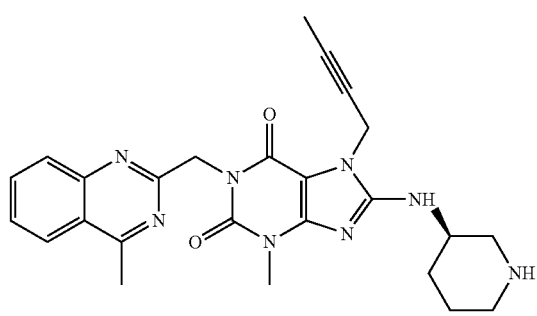
Ib
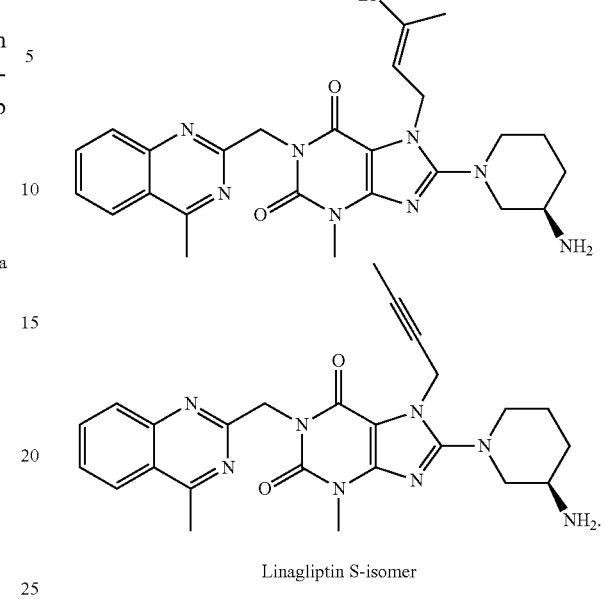
Linagliptin S-isomer
* * * * *